United States Patent
Gaudl et al.

(10) Patent No.: US 9,938,231 B2
(45) Date of Patent: Apr. 10, 2018

(54) LIQUID ARYLBENZOYL BENZOIC ACID ESTER DERIVATIVES FOR ENERGY CURABLE COMPOSITIONS

(71) Applicant: SUN CHEMICAL CORPORATION, Parsippany, NJ (US)

(72) Inventors: Kai-Uwe W. Gaudl, Bavaria (DE); Juergen Dieker, Hesse (DE)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 15/302,683

(22) PCT Filed: Apr. 17, 2015

(86) PCT No.: PCT/US2015/026410
§ 371 (c)(1),
(2) Date: Oct. 7, 2016

(87) PCT Pub. No.: WO2015/164205
PCT Pub. Date: Oct. 29, 2015

(65) Prior Publication Data
US 2017/0029360 A1 Feb. 2, 2017

Related U.S. Application Data

(60) Provisional application No. 61/983,069, filed on Apr. 23, 2014.

(51) Int. Cl.
| | |
|---|---|
| C08F 2/46 | (2006.01) |
| C08F 2/50 | (2006.01) |
| C08G 61/04 | (2006.01) |
| C07C 69/76 | (2006.01) |
| C07C 51/083 | (2006.01) |
| C09D 11/03 | (2014.01) |
| C09D 11/101 | (2014.01) |
| C07C 63/06 | (2006.01) |

(52) U.S. Cl.
CPC ............ *C07C 69/76* (2013.01); *C07C 51/083* (2013.01); *C07C 63/06* (2013.01); *C09D 11/03* (2013.01); *C09D 11/101* (2013.01)

(58) Field of Classification Search
CPC ....... C07C 69/76; C07C 63/06; C07C 51/083; C07C 65/34; C09D 11/101; C09D 11/03

USPC ........ 522/8, 7, 68, 6, 71, 189, 184, 1; 520/1
See application file for complete search history.

(56) References Cited

U.S. PATENT DOCUMENTS

| | | | |
|---|---|---|---|
| 2003/0194384 A1* | 10/2003 | Bonda | A61K 8/35 424/59 |
| 2014/0002534 A1 | 1/2014 | Maeda et al. | |
| 2014/0005332 A1 | 1/2014 | Lindekens et al. | |

FOREIGN PATENT DOCUMENTS

| | | |
|---|---|---|
| WO | WO 2013/107587 A1 | 7/2013 |
| WO | WO 2013/107588 A1 | 7/2013 |
| WO | WO 2015/010729 A1 | 1/2015 |

OTHER PUBLICATIONS

International Search Report issued in International Application No. PCT/US15/26410, dated Aug. 25, 2015.
Written Opinion of the International Searching Authority issued in International Application No. PCT/US15/26410, dated Aug. 25, 2015.

* cited by examiner

*Primary Examiner* — Jessica Whiteley
(74) *Attorney, Agent, or Firm* — Charles C. Achkar; Ostrolenk Faber LLP.

(57) ABSTRACT

4-Arylbenzoyl benzoic acid esters, such as the ethylhexyl esters and amyl esters of 4-phenylbenzoyl benzoic acid, are described, which are liquid and show excellent solubility in acrylic or methacrylic monomers. Compounds of Formula 1, wherein $R^1$, $R^2$, and A are as defined herein, are disclosed. They are suitable as components for radical photoinitiator systems for UV-curable compositions.

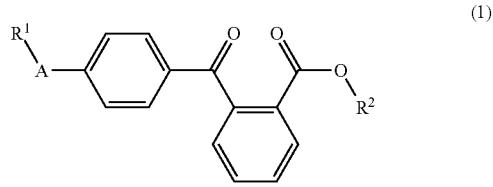

(1)

25 Claims, No Drawings

LIQUID ARYLBENZOYL BENZOIC ACID ESTER DERIVATIVES FOR ENERGY CURABLE COMPOSITIONS

CROSS REFERENCE TO RELATED APPLICATIONS

The present application is a § 371 National Phase application based on PCT/US2015/026410 filed Apr. 17, 2015, which claims the benefit of U.S. Provisional Application No. 61/983,069, filed Apr. 23, 2014 the subject matter of each of which is incorporated by reference in their entirety.

FIELD OF THE INVENTION

The present invention is directed to 4-arylbenzoyl benzoic acid ester derivatives that are liquid at room temperature, and that are suitable as components for radical photoinitiator systems for UV-curable compositions. The photoinitiators of the present invention exhibit excellent solubility in (meth) acrylic monomers.

BACKGROUND

Benzophenone is widely used as a component of photoinitiator systems in UV-curable inks and coatings, especially in combination with aliphatic amines, such as dimethylaminoethanol or aromatic amines, such as dimethylaminobenzoates. However, the UV absorption of benzophenone is at a wavelength too short to give a good match with the emission of typical UV-bulbs, especially when doped UV bulbs are used, which emit at longer wavelengths. Therefore, phenylbenzophenone, which has an extended p-electron system, is often used to increase the absorption wavelength of photoinitiator systems, and to get a better match with UV-bulb emissions.

However, phenylbenzophenone (PBz) is a crystalline solid which exhibits limited solubility in acrylates, and which furthermore has a high melting point, and tends to crystallize from inks, coatings and photoinitiator-blends. This is especially problematic in low viscosity coatings and inks, such as UV-overprint varnishes, UV-flexographic inks and UV-digital inks, in which small molecules crystallize more easily, and product stability is a challenge.

Moreover, it is also a challenge to use phenylbenzophenone at a higher level to provide outstanding UV-cure, because there is then an increased danger of seeding and precipitation, especially in acrylates, which have lower solubility power. Acrylates, such as, for example, propoxylated pentaerythritol tetraacrylate and di-pentaerythritol hexaacrylate, are often key components used to formulate UV-curable flexographic and low migration inks.

EP 2508574 describes radiation curable compositions comprising an ethylencially unsaturated compound (e.g. (meth)acrylate), and inert hydroxyl-terminated polyesters. The inert polyesters may be modified to include moieties possessing photoinitiator activity. The examples describe inert polyesters modified with benzoic acid derivatives.

WO 2015/010729 discloses 4-phenylbenzoyl benzoic acid esters substituted with a residue of a hydroxyl compound having one to six hydroxyl groups. These compounds are useful as photoinitiators in radiation curable compositions.

4-phenylbenzoyl benzoic acid esters have been described in the literature as sun blockers in lotions or protective films (see, for e.g. WO 2010/075946 and DE 3831920). These are generally highly viscous, or solid compositions.

There remains a need to find photoinitiators that can be used in high levels in low viscosity inks and coatings, to promote faster cure speed and an increase in productivity.

SUMMARY OF THE INVENTION

The present invention provides 4-arylbenzoyl benzoic acid esters, such as ethylhexyl esters and amyl esters of 4-arylbenzoyl benzoic acid, which are liquid at room temperature and show excellent solubility in acrylic and methacrylic monomers. These materials are unexpectedly liquid, which is unique because the other known monomeric ester derivatives of arylbenzoyl benzoic acid are solids. They are suitable as components for radical photoinitiator systems for UV-curable compositions.

In a certain aspect, the present invention provides a compound of Formula 1:

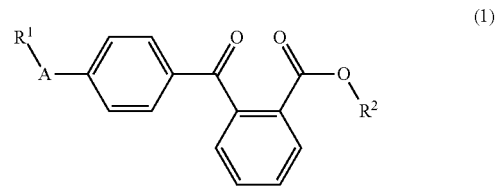

wherein:

A is $C_6$-$C_{22}$ aryl or a (6- to 22-membered) heteroaryl;

$R^1$ is selected from the group consisting of H, $C_1$-$C_8$ alkyl, $C_1$-$C_8$ alkoxy, $C_3$-$C_{22}$ cycloalkyl, a (3- to 22-membered) unsaturated or partially unsaturated heterocyclo, $C_6$-$C_{22}$ aryl, a (6- to 22-membered) heteroaryl, and $NR^3R^4$;

$R^3$ and $R^4$ are each independently selected from H or $C_1$-$C_8$ alkyl; or $R^3$ and $R^4$, together with the nitrogen atom to which they are attached, form a five or six membered ring;

$R^2$ is selected from the group consisting of $C_4$-$C_{22}$ alkyl, $C_7$-$C_{22}$ alkaryl, $C_7$-$C_{22}$ aralkyl, a glycol ether residue comprising a total of between five and twenty two carbon and oxygen atoms, a $C_4$-$C_{22}$ aminoalkyl, and $NR^3R^4$ optionally substituted with $C_1$-$C_8$ alkyl; provided that when A is phenyl and $R^2$ is a glycol ether residue, methyl, ethyl, ethylhexyl, methylheptyl, benzyl, t-butylbenzyl, or methylnaphthyl, then $R^1$ is not H; and provided that when A is phenyl and $R^2$ is t-butyl, then $R^1$ is not methyl.

In a certain embodiment, A is phenyl.

In one embodiment, the compound of Formula 1 is a $C_9$-$C_{22}$ alkyl or aralkyl ester.

In another embodiment, the compound of Formula 1 is a glycol ether ester; provided that if A is phenyl, then $R^1$ is not H.

In another embodiment, the compound of Formula 1 is an alicyclic ester.

In one embodiment, the compound of Formula 1 is a dialkylaminoalkyl ester.

In a certain aspect, the present invention provides the use of one or more compounds of Formula 1 as a component for radical photoinitiator systems for UV-curable inks and coatings.

In one embodiment, the radical photoinitiator system comprises a $C_5$-$C_8$ ester of a compound of Formula 1.

In a particular aspect, the present invention provides a composition comprising at least one compound of Formula 1 and at least one hydrogen radical donor; wherein the composition is liquid at 25° C.

In one embodiment, the composition comprises at least one $C_5$-$C_8$ ester of a compound of Formula 1.

In one embodiment, the composition contains greater than 10 weight % of a $C_5$-$C_8$ ester of a compound of Formula 1.

In another embodiment, the composition comprises a $C_5$-$C_8$ ester of a compound of Formula 1 which is an amyl ester or an ethylhexyl ester.

In one embodiment, the hydrogen donor is a tertiary amine or a thioether.

In one embodiment, the composition comprises at least two compounds of Formula 1, none of which are liquid at 25° C. in its pure form.

In one embodiment, the composition further comprises one or more $C_1$-$C_4$ esters of 4-arylbenzoylbenzoic acid.

In a certain aspect, the present invention provides a coating or printing ink, curable with actinic light, comprising one or more acrylates or methacrylates, a tertiary amine, and at least one compound of Formula 1.

In a certain aspect, the present invention provides a coating or printing ink, curable with actinic light, comprising:
  a) one or more acrylates or methacrylates;
  b) a tertiary amine;
  c) a composition comprising at least one compound of Formula 1 and at least one hydrogen radical donor;
  d) and optionally further comprising one or more $C_1$-$C_4$ esters of 4-arylbenzoylbenzoic acid.

In one embodiment, the coating or printing ink comprises a $C_5$-$C_8$ ester of a compound of Formula 1.

In another embodiment, the coating or printing ink comprises an ethylhexyl ester or an amyl ester of a compound of Formula 1.

In one embodiment, the coating or printing ink contains the acrylates or methacrylates at a concentration of 20-98 weight %.

In a certain aspect, the present invention provides a process for preparation of 4-phenylbenzoyl benzoic acid comprising the steps of:
  a) dispersing or dissolving biphenyl and phthalic anhydride in a molar ratio of 0.95:1 to 1.05:1 in an inert solvent;
  b) feeding aluminum trichloride in molar excess to phthalic anhydride, so that the temperature does not exceed 20° C.;
  c) stirring at 25° C. or above for at least 6 hours;
  d) pouring the reaction mixture in acidified water having a pH<1; and
  e) filtering off the solid precipitate, washing with water, and drying.

In a certain aspect, the present invention provides a composition comprising 4-phenylbenzoyl benzoic acid amyl ester, wherein the composition is liquid at 25° C.

In another embodiment, the present invention provides a composition comprising 4-phenylbenzoyl benzoic acid ethylhexyl ester, wherein the composition is liquid at 25° C.

DETAILED DESCRIPTION OF THE INVENTION

It is to be understood that the foregoing general description and the following detailed description are exemplary and explanatory only, and are not restrictive of any subject matter claimed.

Unless otherwise defined, all technical and scientific terms used herein have the same meaning as is commonly understood by one of skill in the art to which the inventions belong. All patents, patent applications, published applications and publications, websites and other published materials referred to throughout the entire disclosure herein, unless noted otherwise, are incorporated by reference in their entirety for any purpose.

In this application, the use of the singular includes the plural unless specifically stated otherwise. As used herein, the singular forms "a," "an" and "the" are intended to include the plural forms as well, unless the context clearly indicates otherwise.

In this application, the use of "or" means "and/or" unless stated otherwise.

As used herein, the terms "comprises" and/or "comprising" specify the presence of the stated features, integers, steps, operations, elements, and/or components, but do not preclude the presence or addition of one or more other features, integers, steps, operations, elements, components, and/or groups thereof. Furthermore, to the extent that the terms "includes," "having," "has," "with," "composed," "comprised" or variants thereof are used in either the detailed description or the claims, such terms are intended to be inclusive in a manner similar to the term "comprising."

As used herein, ranges and amounts can be expressed as "about" a particular value or range. "About" is intended to also include the exact amount. Hence "about 5 percent" means "about 5 percent" and also "5 percent." "About" means within typical experimental error for the application or purpose intended.

As used herein, the terms "(meth)acrylate" or "(meth) acrylic acid" include both acrylate and methacrylate compounds.

Throughout this disclosure, all parts and percentages are by weight (wt % or mass % based on the total weight) and all temperatures are in ° C. unless otherwise indicated.

As used herein, the term "alkyl" refers to straight chain and branched saturated non-cyclic hydrocarbons, having from 1 to 22 carbon atoms. Representative straight chain alkyl groups include methyl, -ethyl, -n-propyl, -n-butyl, -n-pentyl, -n-hexyl, n-heptyl, n-octyl, n-nonyl, n-decyl, and n-amyl. Representative branched alkyl groups include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 5-methylhexyl, 6-methylheptyl, 2-ethylhexyl, and the like.

As used herein, the term "alkoxy" means a straight chain or branched non-cyclic hydrocarbon having one or more ether groups and from 1 to 22 carbon atoms. Representative straight chain and branched alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like.

As used herein, the term "amino" refers to —$NH_2$.

As used herein, the term "aminoalkyl" refers to an alkyl group substituted by an amino group.

As used herein, the term "aryl" means an aromatic carbocyclic ring containing 6 to 22 carbon atoms, including both mono-, bi-, and tricyclic ring systems. Representative aryl groups include -indenyl, -phenyl, -naphthyl, anthracenyl and the like.

As used herein, the term "heteroaryl" means an aromatic heterocycle ring of 6 to 22 members, including both mono- and bicyclic ring systems, where at least one carbon atom (of one or both of the rings) is replaced with a heteroatom independently selected from nitrogen, oxygen, and sulfur, or at least two carbon atoms of one or both of the rings are replaced with a heteroatom independently selected from nitrogen, oxygen, and sulfur. Representative heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, thiadiazolyl, cinnolinyl, phthalazinyl, quinazolinyl, and the like.

As used herein, "heterocycle" or "heterocycle ring" refers to a 3- to 22-membered monocyclic heterocyclic ring which is either unsaturated or partially saturated. A 3-membered heterocycle can contain up to 1 heteroatom; a 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The heterocycle can be attached via a nitrogen or carbon atom. Representative heterocycles include thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiopyranyl, and the like.

As used herein, the term "cycloalkyl" refers to a cyclic saturated hydrocarbon having from 3 to 22 carbon atoms. Representative cycloalkyls include cyclopropyl, cyclobutyl, cyclopentyl, cyclohexyl, cycloheptyl, cyclooctyl, and cyclononyl, cyclodecyl, cycloundecyl, cyclododecyl, and the like.

As used herein, the term "alkaryl" refers to an aryl radical substituted with one, two or three alkyl groups.

As used herein, the term "aralkyl" refers to an alkyl radical substituted with one, two or three optionally substituted aryl groups. Non-limiting examples of aralkyl groups include benzyl and phenethyl.

As used herein, "optionally substituted" refers to a group that is either unsubstituted or substituted.

In a certain aspect, the present invention provides a compound of Formula 1:

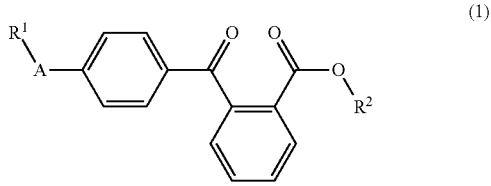

(1)

wherein:
A is $C_6$-$C_{22}$ aryl or a (6- to 22-membered) heteroaryl;
$R^1$ is selected from the group consisting of H, $C_1$-$C_8$ alkyl, $C_1$-$C_8$ alkoxy, $C_3$-$C_{22}$ cycloalkyl, a (3- to 22-membered) unsaturated or partially unsaturated heterocycle, $C_6$-$C_{22}$ aryl, a (6- to 22-membered) heteroaryl, and $NR^3R^4$;

$R^3$ and $R^4$ are each independently selected from H or $C_1$-$C_8$ alkyl; or $R^3$ and $R^4$, together with the nitrogen atom to which they are attached, form a five or six membered ring;
$R^2$ is selected from the group consisting of $C_4$-$C_{22}$ alkyl, $C_7$-$C_{22}$ alkaryl, $C_7$-$C_{22}$ aralkyl, a glycol ether residue comprising a total of between five and twenty two carbon and oxygen atoms, a $C_4$-$C_{22}$ aminoalkyl, and $NR^3R^4$ optionally substituted with $C_1$-$C_8$ alkyl; provided that when A is phenyl and $R^2$ is a glycol ether residue, methyl, ethyl, ethylhexyl, methylheptyl, benzyl, t-butylbenzyl, or methylnaphthyl, then $R^1$ is not H; and provided that when A is phenyl and $R^2$ is t-butyl, then $R^1$ is not methyl.

In non-limiting examples, $R^1$ may be attached to A at the ortho, meta, or para positions.

The liquid 4-arylbenzoyl benzoic acid esters of the present invention are suitable as photoinitiator components in formulations with low viscosity. Formulations comprising the 4-arylbenzoyl benzoic acid esters of the present invention have good product stability. Moreover, the compounds of the invention have improved solubility in monomers that are critical for the formulation of flexographic and low migration inks and coatings, such as (meth)acrylates (e.g. propoxylated pentaerythritol tetraacrylate and di-pentaerythritol hexaacrylate).

Because the compounds of the invention are liquid, a higher amount of photoinitiator can be used in the formulation of inks and coatings, without seeding and precipitation of the photoinitiator. This allows for faster processing speeds, and higher productivity.

It has now been found that one suitable 4-arylbenzyl benzoic acid ester is 4-phenylbenzoyl benzoic acid ethylhexyl ester. This has previously only been described as a sun blocker in protective films, and in sun-creams and lotions. Its use as a photoinitiator in radiation curable compositions has hitherto been unknown.

The inventors have now found that the 4-arylbenzyl benzoic acid esters of the invention can also be used in combination with a hydrogen donor, to make radical photoinitiator solutions for coating and ink compositions. The coatings and inks exhibit a low viscosity and good stability.

4-Arylbenzoyl benzoic acids in general can be made by reacting an aromatic compound such as biphenyl or substituted biphenyls in an, for this reaction, inert solvent, such as for example methylene dichloride or dichloroethane, in the presence of a Lewis acid, suitable as a Friedl-Crafts acylation reagent, usually aluminum trichloride.

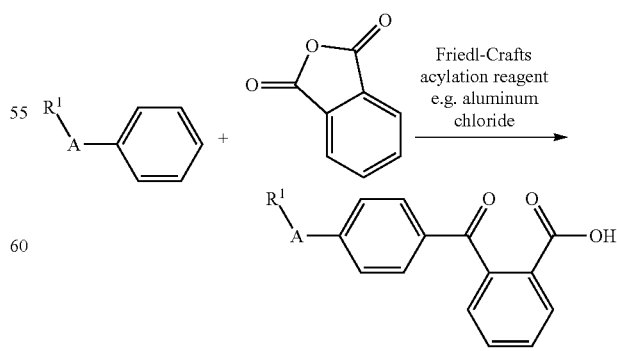

4-Arylbenzoyl benzoic acids esters can be made by esterifying 4-arylbenzoyl benzoic acids with an alcohol such as methanol, ethanol, propanol, isopropanol, butanol, isobutanol, amyl alcohols, hexanol, heptanol, ethylhexanol or higher alcohols. In order to obtain a fast establishment of the equilibrium in the esterification reaction, a strong acid can be used in 0.5-5.0 weight %, such as toluene sulfonic acid, methane sulfonic acid, or sulfuric acid. Additionally, an entrainer, such as cyclohexane, toluene, or xylene, can be used to remove water from the reaction mixture, and drive the reaction to completion. Alternatively, an excess of alcohol can be used.

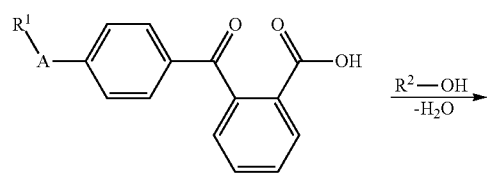

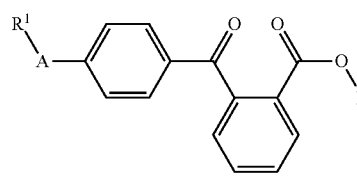

Surprisingly, among the known esters of 4-phenylbenzoyl benzoic acid, the ethylhexyl ester as well the amyl ester are somewhat special in that they are liquid at about room temperature. Lower esters, such as for example 4-phenylbenzoyl benzoic acid methyl ester (melting point 225° C.), as well as the higher known esters such as 4-phenylbenzoyl benzoic acid benzyl ester, are crystalline solids and tend to precipitate out of solution.

4-Phenylbenzoyl benzoic acid ethylhexyl ester and 4-phenylbenzoyl benzoic acid amyl ester can be made from biphenyl and phthalic anhydride by Friedel-Crafts acylation, followed by esterification with ethylhexanol or amylalcohol. The general reaction scheme is:

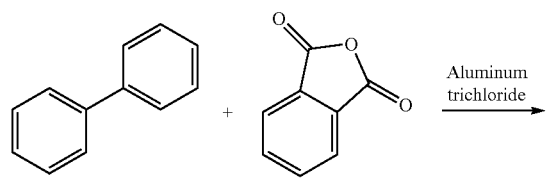

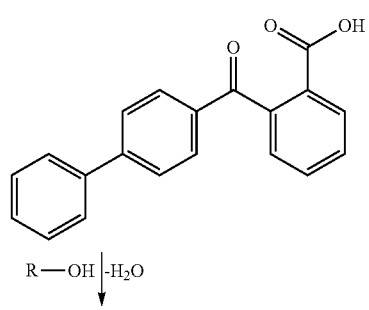

-continued

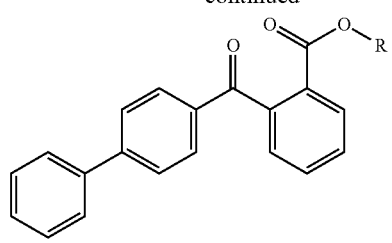

The inventors also developed a procedure in which the intermediate 4-phenylbenzoyl benzoic acid directly precipitates in excellent purity when poured into water and can be separated by filtration. Thus, a purification via a carboxylic acid salt in an aqueous medium, usually described in the prior art, is no longer required.

Usually, the Friedel-Crafts acylation is done in an inert solvent, such as methylene chloride, chloroform, tetrachloro methane, nitrobenzene, dichlorobenzene, or the like. A suitable amount of solvent is >20% and the molar ratio of biphenyl and phthalic anhydride is 0.95:1 to 1.05:1. Preferred is a slight excess of biphenyl to complete the consumption of anhydride. In the process of the present invention, aluminum trichloride is used in molar excess to provide excellent yield. The aluminum trichloride is preferably added in portions under water cooling, so that the temperature does not exceed room temperature, and preferably stirred at room temperature for at least 6 hours. Then, the blue-brown reaction mixture is poured into acidified water, where the product immediately precipitates. Then the product is separated by filtration, washed and dried, and obtained as a colorless solid, preferably having a purity of >96%, measured with gas chromatography and liquid chromatography, in an almost quantitative yield.

For the second step, the esterification, usually an acid catalyst, such as methane sulfonic acid or sulfuric acid, or a metal catalyst, such as titanium tetrabutylate or butyl tin hydroxyl-oxide, is suitable at a preferred level of 0.1 to 5.0 weight %. The formed water can be removed physically by the help of an entrainer such as xylene, a nitrogen gas stream or vacuum.

Alternatively, the esterification can be done by making an acid chloride with for example thionyl chloride and esterify under milder conditions.

Another preferred embodiment of the compound of Formula 1 contains a terphenyl group in the photoinitiator wherein $R^1$ is phenyl.

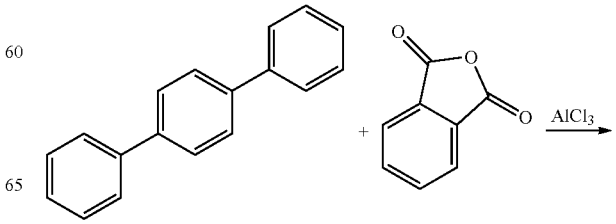

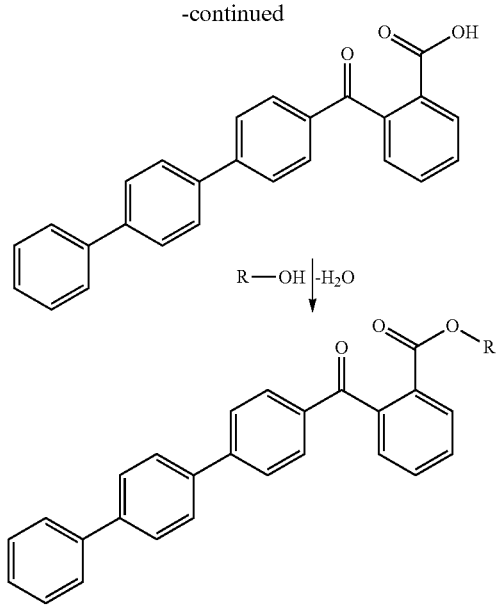

By enhancing the conjugated π-electron system from a biphenyl to a terphenyl photoinitiator, both absorption maximum wavelength and molar extinction coefficient increase. The increased absorption wavelength is important to give a better fit with the emission spectra of new types of low energy ozone-free UV-bulbs which have emerged during the last years. In low energy, usually iron doped UV-bulbs, the emission spectrum is shifted to longer wavelengths.

However, the most important feature of the terphenyl photoinitiators is the increased molar extinction coefficient. It is very important in highly pigmented systems, so that the pigment light absorption does not completely cover the absorption of the photo initiator, which would lead to poor cure.

Moreover, it is known in the art that a low extinction coefficient in photoinitiators results in inefficient light absorption, and therefore weaker formation of radicals, giving poorer cure. ("Photoinitiator for free radical, cationic & anionic photopolymerization", K. Dietlieker et al., Wiley & Sons, 1998, ISBN 0471 978922, page 97).

Therefore, the inventive photoinitiators of this invention containing a terphenyl group having a high extinction coefficient are especially advantageous for curing highly pigmented printing inks, especially when cured with low energy UV-bulbs.

| Material | Absorption maximum [nm] | Molar extinction coefficient [liter · mol$^{-1}$ · cm$^{-1}$] |
|---|---|---|
| 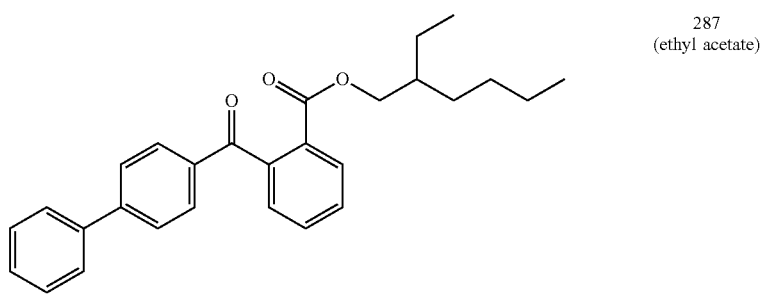  example 9 | 287 (ethyl acetate) | 20100 |
| example 12 | 309 (ethyl acetate) | 24900 |

4-Phenylbenzoyl benzoic acid ethylhexyl ester and 4-phenylbenzoyl benzoic acid amyl ester are especially useful for formulating highly reactive UV-curable compositions, for example UV-flexographic inks and coatings, UV-digital inks and coatings, and UV-inks and coatings curable with low energy UV-bulbs, because the active photoinitiator species can be used in high levels without the risk of separation, seeding or the like.

In contrast to 4-phenylbenzophenone, 4-phenylbenzoyl benzoic acid ethylhexyl ester and 4-phenylbenzoyl benzoic acid amyl ester show excellent solubility in (meth)acrylic monomers and oligomers which are critical to formulate UV-flexographic inks and UV low migration inks and coatings. Examples of these acrylic monomers are propoxylated pentaerythritol tetraacrylate (PPTTA) or di-pentaerythritol hexaacrylate (DPHA) (see Tables 1 and 2).

Moreover, the molecular weight of 4-phenylbenzoyl benzoic acid ethylhexyl ester is increased by more than one third over phenylbenzophenone, so that the ability to migrate is lowered, because the tendency of a molecule to migrate is a function of molecular weight ((L. L. Katan in "Migration of additive food contact", Black Academical & Professional, first edition, London 1996, page 97, table 5.3). Surprisingly, despite the increased molecular weight of 4-phenylbenzoyl benzoic acid ethylhexyl ester vs. phenylbenzophenone, there was no significant decrease in reactivity in the curable compositions (see Tables 3 and 4).

The UV-curable compositions of the present invention preferably contain at least one acrylate or methacrylate, one hydrogen radical donor such as an amine or thioether, and a photoinitiator compound of Formula 1:

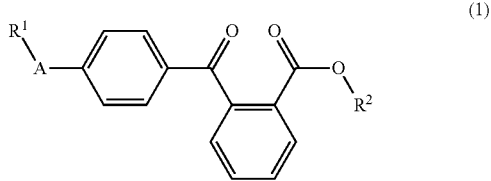

(1)

wherein:
A is $C_6$-$C_{22}$ aryl or a (6- to 22-membered) heteroaryl;
$R^1$ is selected from the group consisting of H, $C_1$-$C_8$ alkyl, $C_1$-$C_8$ alkoxy, $C_3$-$C_{22}$ cycloalkyl, a (3- to 22-membered) unsaturated or partially unsaturated heterocycle, $C_6$-$C_{22}$ aryl, a (6- to 22-membered) heteroaryl, and $NR^3R^4$;
$R^3$ and $R^4$ are each independently selected from H or $C_1$-$C_8$ alkyl; or $R^3$ and $R^4$, together with the nitrogen atom to which they are attached, form a five or six membered ring;
$R^2$ is selected from the group consisting of $C_4$-$C_{22}$ alkyl, $C_7$-$C_{22}$ alkaryl, $C_7$-$C_{22}$ aralkyl, a glycol ether residue comprising a total of between five and twenty two carbon and oxygen atoms, a $C_4$-$C_{22}$ aminoalkyl, and $NR^3R^4$ optionally substituted with $C_1$-$C_8$ alkyl; provided that when A is phenyl and $R^2$ is a glycol ether residue, methyl, ethyl, ethylhexyl, methylheptyl, benzyl, t-butylbenzyl, or methylnaphthyl, then $R^1$ is not H; and provided that when A is phenyl and $R^2$ is t-butyl, then $R^1$ is not methyl.

A most preferred embodiment of this invention contains at least one acrylate or methacrylate, one hydrogen radical donor such as an amine or thioether, and a $C_5$-$C_8$ ester of 4-phenylbenzoylbenzoic acid.

A non-limiting list of examples of acrylates suitable in the radiation curable compositions of the present invention include ethylene glycol diacrylate, 1,4-butandiol diacrylate, 1,6-hexandiol diacrylate, dipropylene glycol diacrylate, neopentylglycol diacrylate, ethoxylated neopentylglycol diacrylates, propoxylated neopentylglycol diacrylates, tripropylene glycol diacrylate, bisphenol-A diacrylate, ethoxylated bisphenol-A-diacrylates, bisphenol-A-diglycidylether diacrylate, ethoxylated bisphenol-A-diacrylates, poly(ethylene) glycol diacrylates, trimethylolpropane triacrylate, trimethylolpropane trimethacrylate, ethoxylated trimethylolpropane triacrylates, propoxylated trimethylolpropane triacrylates, propoxylated glycerol triacrylates, pentaerythritol triacrylate, ethoxylated pentaerythritol triacrylates, propoxylated pentaerythritol tetraacrylates, ethoxylated pentaerythritol tetraacrylates, ditrimethylolpropane tetraacrylate, dipentaerythritol pentaacrylate, dipentaerythritol hexaacrylate or mixtures thereof, preferred are ethoxylated trimethylolpropane triacrylates, ethoxylated pentaerythritol triacrylates and propoxylated pentaerythritol tetraacrylates, oligomeric and polymeric acrylates applied in the art, such as for example epoxy acrylates, polyester acrylates, acrylated polyurethanes, acrylated polyacrylates, acrylated polyethers, acrylated epoxidized oils based on linseed oil and soybean oil, mixtures thereof, and the like.

A non-limiting list of examples of suitable methacrylates are ethylene glycol dimethacrylate, 1,4-butandiol dimethacrylate, 1,6-hexandiol dimethacrylate, dipropylene glycol dimethacrylate, neopentylglycol dimethacrylate, ethoxylated neopentylglycol dimethacrylates, propoxylated neopentylglycol dimethacrylates, tripropylene glycol dimethacrylate, bisphenol-A dimethacrylate, ethoxylated bisphenol-A-dimethacrylates, bisphenol-A-diglycidylether dimethacrylate, ethoxylated bisphenol-A-dimethacrylates, poly(ethylene)glycol dimethacrylates, trimethylolpropane trimethacrylate, ethoxylated trimethylolpropane trimethacrylates, propoxylated trimethylolpropane trimethacrylates, propoxylated glycerol trimethacrylates, pentaerythritol trimethacrylate, ethoxylated pentaerythritol trimethacrylates, propoxylated pentaerythritol tetramethacrylates, ethoxylated pentaerythritol tetramethacrylates, ditrimethylolpropane tetramethacrylate, dipentaerythritol pentamethacrylate, dipentaerythritol hexamethacrylate or mixtures thereof, preferably ethoxylated trimethylolpropane trimethacrylates, ethoxylated pentaerythritol trimethacrylates and propoxylated pentaerythritol tetramethacrylates, mixtures thereof, and the like.

Suitable amines are, for example, dimethylethanolamine, diethanolmethylamine, N,N-dimethylaminobenzoic acid ethyl ester, N,N-dimethylaminobenzoic acid amyl ester, N,N-dimethylaminobenzoic acid ethylhexyl ester, 4,4'-bis (diethylamino) benzophenone, N-methylcarbazol, oligomeric amines such as Genopol AB (product of Rahn group) and acrylated amines such as adducts of multifunctional acrylates with secondary amines, or Laromer PO94 (Product of BASF).

The radiation curable compositions of the present invention can be cured by an actinic light source, such as UV-light, provided by a high-voltage mercury bulb, a medium-voltage mercury bulb, a xenon bulb, a carbon arc lamp, a metal halide bulb, and especially with an UV-LED lamp or sunlight. The wavelength of applied irradiation is preferably within a range of 250 to 400 nm, more preferably 280-370 nm.

In order to fine-tune properties, the radiation curable composition of the present invention may optionally contain small amounts of additional type-1 and type-2 photoinitiators, such as, for example, benzophenones, benzilketales, dialkoxy acetophenones, hydroxyalkylacetophenones, acylphosphinoxides and thioxanthones. Example include benzophenone, methylbenzophenone, 2,2-dimethoxy-2-phenylacetophenone, dimethoxyacetophenone, diethoxyacetophenone, 2-hydroxy-2-methyl-1-phenylpropan-1-one, 2-benzyl-2-dimethyl amino-1-(4-morpholinophenyl)-butan-1-one, 2-methyl-1-[4(methoxythio)-phenyl]-2-morpholinopropan-2-one, diphenylacylphenyl phosphinoxide, diphenyl(2,4,6-trimethylbenzoyl) phosphinoxide, 2,4,6-trimethylbenzoylethoxyphenyl phosphinoxide, 2-isopropylthioxanthone, 4-isopropylthioxanthone, 2,4-dimethylthioxanthone and their oligomeric counterparts.

Besides the use as a component of radical photoinitiator systems for UV curable compositions, esters of 4-arylbenzoyl benzoic acid, especially the $C_5$-$C_8$ esters, as liquids, dissolve a variety of other photoinitiators, co-initiators and synergists, and are therefore also suitable to render photoinitiator blends liquid and stable. This is shown in Table 5. It should also be noted that combinations of esters of 4-arylbenzoylbenzoic acids, for example mixtures of the various butyl esters of 4-phenylbenzoylbenzoic acid, can together yield a mixture of photoinitiators that has a melting point below 25° C. even though the individually pure materials have melting points above 25° C. Thus, such a combination of photoinitiators can also function as a liquid to dissolve a variety of other photoinitiators, co-initiators, and synergists.

4-Phenylbenzoyl benzoic acid ethylhexyl ester and 4-phenylbenzoyl benzoic acid amyl ester are useful as components in radical photoinitiator systems, for UV-curable compositions as well as a component for liquid photoinitiator blends. They exhibit excellent solubility in a variety of acrylic monomers and oligomers suitable to make UV-curable coatings and inks.

Although the photoinitiators of the present application are exemplified using non-pigmented coatings, one of skill in the art would recognize that they could easily be used in colored inks and coatings as well.

Suitable colorants include, but are not limited to organic or inorganic pigments and dyes. The dyes include but are not limited to azo dyes, anthraquinone dyes, xanthene dyes, azine dyes, combinations thereof and the like. Organic pigments may be one pigment or a combination of pigments, such as for instance Pigment Yellow Numbers 12, 13, 14, 17, 74, 83, 114, 126, 127, 174, 188; Pigment Red Numbers 2, 22, 23, 48:1, 48:2, 52, 52:1, 53, 57:1, 112, 122, 166, 170, 184, 202, 266, 269; Pigment Orange Numbers 5, 16, 34, 36; Pigment Blue Numbers 15, 15:3, 15:4; Pigment Violet Numbers 3, 23, 27; and/or Pigment Green Number 7. Inorganic pigments may be one of the following non-limiting pigments: iron oxides, titanium dioxides, chromium oxides, ferric ammonium ferrocyanides, ferric oxide blacks, Pigment Black Number 7 and/or Pigment White Numbers 6 and 7. Other organic and inorganic pigments and dyes can also be employed, as well as combinations that achieve the colors desired.

As with most printing inks, other additives, alone or in combination, may be employed, including but not limited to, waxes, ammonia, defoamers, dispersants, stabilizers, silicones, rheological modifiers, plasticizers and the like.

EXAMPLES

The following examples illustrate specific aspects of the present invention and are not intended to limit the scope thereof in any respect and should not be so construed. Unless otherwise indicated, the test methods were as described below.

UV-Spectra Measurement:

Spectra were acquired using a Unicam UV-2 UV/VIS spectrophotometer. All absorption spectra were obtained using 1 cm cuvettes, scanning within the 200-800 nm range. Solutions were prepared in a 100 $cm^3$ volumetric flask, and if required, subsequently diluted so that a maximum absorbance of less than 2 was obtained. From the absorption spectra, the molar extinction coefficient e was calculated in liter·$mol^{-1}$·$cm^{-1}$.

Melting Point:

Melting points were determined by a calibrated Büchi melting point apparatus.

FTIR Spectra Measurement:

The Fourier transform infrared (FTIR) spectra were recorded on a Bio-Rad Excalibur FTS 3000 spectrophotometer using a surface reflectance method (solid samples, Golden Gate single reflection diamond attenuated total reflectance accessory).

Assessment of Cure:
 a) Film hardness: The thumb is pressed on the surface of the cured coating and rotated for 90°. If no marks are left on the surface, the cure is regarded as "OK".
 b) Solvent resistance: Higher crosslinked materials pose a better resistance to solvents. A cotton-tipped plastic stick is soaked with acetone or alcohol and rubbed over the cured coating or ink. The more rubs the cured coating or ink withstands without being destroyed, the better rated the cure is. Acetone is typically more aggressive than alcohol.

Example 1: Solubility of 4-Arylbenzoyl Benzoic Acid Esters in Propoxylated Pentaerythritol Tetraacrylate 4-phenylbenzophenone, 4-phenylbenzoyl benzoic acid ethylhexyl ester, and 4-phenylbenzoyl benzoic acid amyl ester were each separately added to the multifunctional acrylate propoxylated pentaerythritol tetraacrylate (SR 494 LM, Sartomer company) (PPTTA) in amounts of 2, 4, 6, and 8 weight % and stirred for 30 minutes at room temperature. The results are shown in Table 1.

TABLE 1

Solubility in propoxylated pentaerythritol tetraacrylate SR 494 LM (PPTTA)

| Mixture | Benzophenone Derivative | Concentration [weight %] in PPTTA | | | |
|---|---|---|---|---|---|
| | | 2% | 4% | 6% | 8% |
| Example 1 (comparative-4-phenyl benzophenone) | 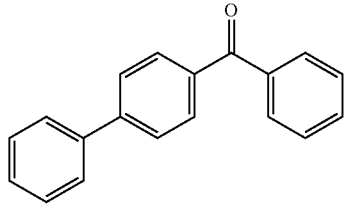 [SMILES: O=C(c1ccccc1)c1ccc(-c2ccccc2)cc1] | solution | hazy | Solid residuals | Solid residuals |
| Example 9 (inventive-4-phenylbenzoyl benzoic acid ethylhexyl ester) | 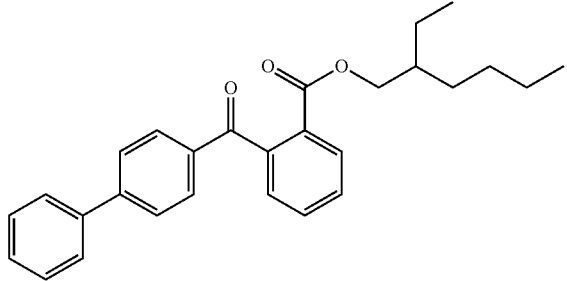 [SMILES: CCCCC(CC)COC(=O)c1ccccc1C(=O)c1ccc(-c2ccccc2)cc1] | solution | solution | solution | solution |
| Example 10 (inventive-4-phenylbenzoyl benzoic acid amyl ester) | 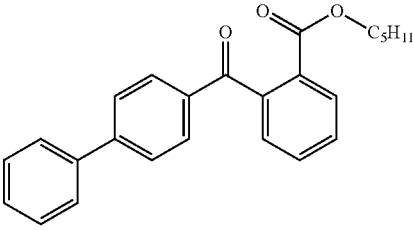 | solution | solution | solution | solution |

4-Phenylbenzoyl benzoic acid ethylhexyl ester and 4-phenylbenzoyl benzoic acid amyl ester both showed better solubility than 4-phenyl benzophenone in propoxylated pentaerythritol tetraacrylate (PPTTA).

Example 2: Solubility of 4-Arylbenzoyl Benzoic Acid Esters in Acrylate Di-Pentaerythritol Hexaacrylate 4-phenylbenzophenone, 4-phenylbenzoyl benzoic acid ethylhexyl ester, and 4-phenylbenzoyl benzoic acid amyl ester were each added separately to the multifunctional acrylate di-pentaerythritol hexaacrylate (DPHA, Miwon Company) in amounts of 2, 4, 6, and 8 weight %, and stirred for 30 minutes at room temperature.

TABLE 2

Solubility in di-pentaerythritol hexaacrylate (DPHA)

| Mixture | Benzaphenone Derivative | Concentration [weight %] in DPHA | | | |
|---|---|---|---|---|---|
| | | 2% | 4% | 6% | 8% |
| Example 1 (comparative) | 4-phenylbenzophenone (structure) | solution | solution | Hazy-opaque | Solid residuals |
| Example 9 (inventive) | 4-phenylbenzoyl benzoic acid ethylhexyl ester (structure) | solution | solution | solution | solution |
| Example 10 (inventive-4-phenylbenzoyl benzoic acid amyl ester) | 4-phenylbenzoyl benzoic acid amyl ester (structure, $C_5H_{11}$) | solution | solution | solution | solution |

4-Phenylbenzoyl benzoic acid ethylhexyl ester and 4-phenylbenzoyl benzoic acid amyl ester showed better solubility than 4-phenyl benzophenone in DPHA.

Examples 3 and 4: Reactivity of 4-Arylbenzoyl Benzoic Acid Esters

Mixtures of each of 4-phenylbenzoyl benzoic acid ethylhexyl ester (Example 3a), 4-phenylbenzoyl benzoic acid amyl ester (Example 3b) and phenylbenzophenone (Example 4) were mixed with dimethylaminobenzoic acid ethylhexyl ester and trimethylol propane triacrylate (Sartomer SR 351). The resulting coating mixtures were low viscosity, exhibiting a viscosity of 100-120 mPas. Viscosity was determined with a Physika 300 cone and plate rheometer from Anton Parr GmbH at a shear rate of D=2 to 100 s-1. The viscosity value at a shear rate of D=50 l/s was recorded. The coating mixtures were applied on a coated "Byk" cardboard test chart (black and white areas) with a wire applicator (10 μm wet) and cured with a medium pressure mercury bulb (Fusion H-bulb (187 W/cm)) and at a conveyor speed of 16-64 meter/minute. Cure was assessed by the solvent resistance test (over black and white), and the thumb twist test. The results are shown in Tables 3a, 3b, and 4.

Inventive Example 3a 4.0 g 4-phenylbenzoyl benzoic acid ethylhexyl ester
4.0 g of dimethylaminobenzoic acid ethylhexyl ester
100 g of trimethylol propane triacrylate TABLE 3a Cure performance of Inventive Example 3a (4-phenylbenzoyl benzoic acid ethylhexyl ester).

| | Conveyor speed [m/min] | | | | | |
|---|---|---|---|---|---|---|
| | 16 | 32 | 48 | 64 | 64 | 64 |
| | Bulb Energy [%] | | | | | |
| | 100 | 100 | 100 | 100 | 50 | 30 |
| Solvent resistance over white [acetone double rubs] | >40 | >40 | >40 | >40 | ~40 | ~7 |

TABLE 3a-continued

Cure performance of Inventive Example 3a (4-phenylbenzoyl benzoic acid ethylhexyl ester).

| | Conveyor speed [m/min] | | | | | |
|---|---|---|---|---|---|---|
| | 16 | 32 | 48 | 64 | 64 | 64 |
| | | | | Bulb Energy [%] | | |
| | 100 | 100 | 100 | 100 | 50 | 30 |
| Solvent resistance over black [acetone double rubs] | >40 | >40 | >40 | >40 | ~35 | ~8 |
| Thumb twist test | pass | pass | Failed (fingerprint left on surface) | Failed (fingerprint left on surface) | Failed (surface smeary) | Failed (surface smeary) |

Inventive Example 3b 4.0 g 4-phenylbenzoyl benzoic acid amyl ester
4.0 g dimethylaminobenzoic acid ethylhexyl ester
100 g trimethylol propane triacrylate TABLE 3b Cure performance of Inventive Example 3b (4-phenylbenzoyl benzoic acid amyl ester).

| | Conveyor speed [m/min] | | | | | |
|---|---|---|---|---|---|---|
| | 16 | 32 | 48 | 64 | 64 | 64 |
| | | | | Bulb Energy [%] | | |
| | 100 | 100 | 100 | 100 | 50 | 30 |
| Solvent resistance over white [acetone double rubs] | >40 | >40 | >40 | >40 | ~40 | ~4 |
| Solvent resistance over black [acetone double rubs] | >40 | >40 | >40 | >40 | ~20 | ~3 |
| Thumb twist test | pass | pass | Failed (fingerprint left on surface) | Failed (fingerprint left on surface) | Failed (surface smeary) | Failed (surface smeary) |

Comparative Example 4

4.0 g 4-phenylbenzophenone
4.0 g of dimethylaminobenzoic acid ethylhexy lester
100 g of trimethylol propane triacrylate

TABLE 4

Cure performance of Comparative Example 4.

| | Conveyor speed [m/min] | | | | | |
|---|---|---|---|---|---|---|
| | 16 | 32 | 48 | 64 | 64 | 64 |
| | | | | Bulb Energy [%] | | |
| | 100 | 100 | 100 | 100 | 50 | 30 |
| Solvent resistance over white [acetone double rubs] | >40 | >40 | >40 | >40 | ~40 | ~10 |
| Solvent resistance over black [acetone double rubs] | >40 | >40 | >40 | >40 | ~35 | ~11 |
| Thumb twist test | pass | pass | Failed (fingerprint left on surface) | Failed (fingerprint left on surface) | Failed (surface smeary | Failed (surface smeary |

As indicated aforementioned, the experiments show that surprisingly, despite the increased molecular weight of 4-phenylbenzoyl benzoic acid ethylhexyl ester and 4-phenylbenzoyl benzoic acid amyl ester compared to 4-phenylbenzophenone, the curing result of the curable compositions containing 4-phenylbenzoyl benzoic acid ethylhexyl ester and 4-phenylbenzoyl benzoic acid amyl ester were almost identical to the compositions containing 4-phenylbenzophenone.

Examples 5-7: Solubility Stability of Photoinitiator Blends

A 1:1 mixture in weight of 4-phenylbenzoyl benzoic acid ethylhexyl ester and dimethylaminobenzoic acid ethylhexyl ester was transformed into a solution by stirring at room temperature. The solution also stayed liquid at 5° C. As a comparison experiment, a 1:1 mixture of 4-phenylbenzophenone and dimethylaminobenzoic acid ethylhexyl ester was turned into a solution at elevated temperature of 50° C. Upon cooling to room temperature, the phenylbenzophenone precipitated. A similar instability and precipitation as with 4-phenyl benzophenone was also observed with 4-phenylbenzoyl benzoic acid methyl ester.

Table 5 shows the unique character of 4-phenylbenzoyl benzoic acid ethylhexyl ester and 4-phenylbenzoyl benzoic acid amyl ester, which are useful to solubilize photoinitiator blends containing solid photoinitiators. Preferably, at least 10 weight % of 4-phenylbenzoyl benzoic acid ethylhexyl ester or 4-phenylbenzoyl benzoic acid amyl ester, preferably 20-50 weight %, are suitable to turn a solid photoinitiator blend into a solution.

Example 8: Synthesis of 4-Phenylbenzoyl Benzoic Acid 154.0 g (1.0 mole) of biphenyl and 148.0 g (1.0 mole) phthalic anhydride were dispersed in 800 ml of methylene

TABLE 5

Solubility stability of photoinitiator blends

| Blend | Benzophenone derivative | Aminobenzoate | Stability at 25° C. | Stability at 5° C. |
|---|---|---|---|---|
| Example 5 (comparative) | 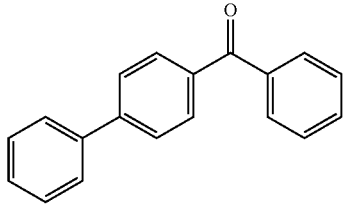 [SMILES: O=C(c1ccccc1)c1ccc(-c2ccccc2)cc1] 50% | 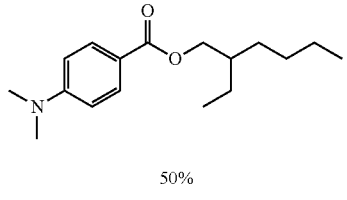 50% | Precipitation of crystals | Precipitation of crystals |
| Example 6* (comparative) | 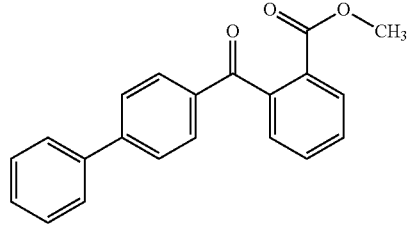 [SMILES: COC(=O)c1ccccc1C(=O)c1ccc(-c2ccccc2)cc1] 50% | 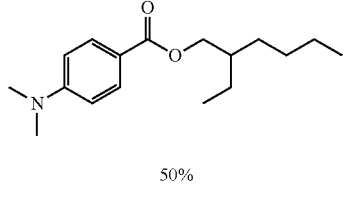 50% | Precipitation of crystals | Precipitation of crystals |
| Example 7 (inventive) | 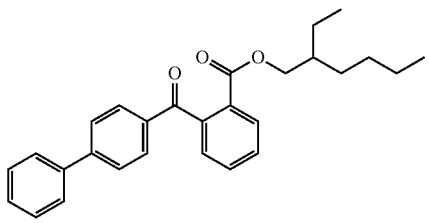 [SMILES: CCCCC(CC)COC(=O)c1ccccc1C(=O)c1ccc(-c2ccccc2)cc1] 50% | 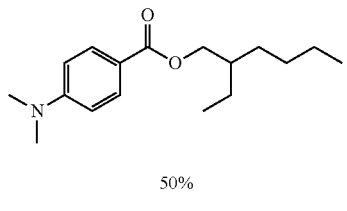 50% | Stable solution (no precipitation) | Stable solution (no precipitation) |
| Example 10 | 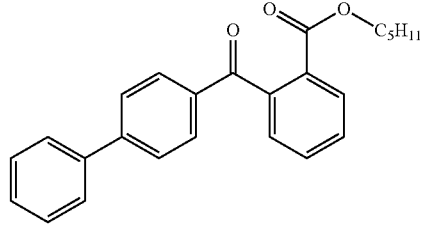 50% | 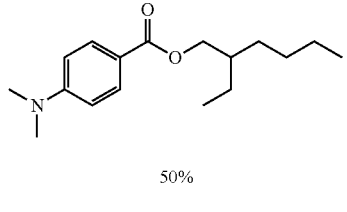 50% | Stable solution (no precipitation) | Stable solution (no precipitation) |

*prepared using the same procedure as described in Example 9 dichloride. Then 226.0 g (2 moles) of aluminum trichloride was added in portions, under water cooling, so that the temperature did not exceed 20° C. Then the mixture was allowed to stir overnight at room temperature and became a greenish-bluish color. Then the reaction mixture was poured slowly, under stirring, into a mixture of 3.0 liters of water, 500 g of crushed ice, and 400 g of sulfuric acid. During the addition, the bluish color disappeared and a white precipitate was formed, which was separated by filtration, washed with 4×300 ml of water, and dried.
Yield: 291.0 g (96% of theory)

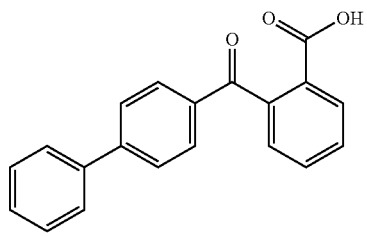 [SMILES: O=C(O)c1ccccc1C(=O)c1ccc(-c2ccccc2)cc1]

Characterization:
GC-purity: 98%
Melting point: 232-233° C.
GC-purity: 99%
Mass Spectroscopy (m/z): 374 (M(+)–1+73(trimethylsilane) 359 (100%), 285,228, 181, 152, 73
UV-spectroscopy: λ max=286 nm (ethanol)

Example 9 (Inventive)

Synthesis of 4-Phenylbenzoyl Benzoic Acid Ethyl Hexyl Ester 30.2 g (0.1 mole) of 4-phenylbenzoyl benzoic acid from Example 8 was mixed with 26.0 g (0.2 moles) of ethylhexanol, 50 ml of toluene, and 2.0 g of toluene sulfonic acid. The mixture was heated to reflux and, within 3 hours, 3 ml of water was separated, and the acid value dropped below 5 mg KOH/g. The mixture was allowed to cool down to room temperature, diluted with 50 ml of methylene dichloride, and extracted three times with 100 ml of saturated sodium bicarbonate solution. Then the solvents were removed by rotary evaporator at 80° C. (50 hPa). Then the excess of ethylhexanol was removed under reduced pressure of 0.1 hPa at a temperature of 120° C. A light brown clear liquid remained.
Yield: 38.1 g (91% of theory)

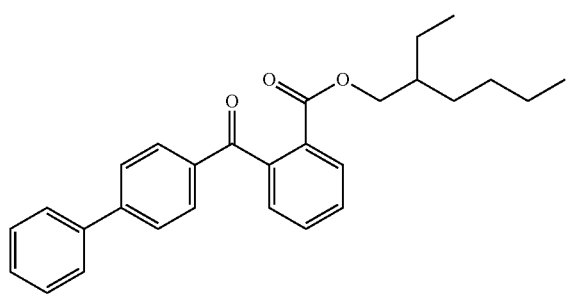 [SMILES: CCCCC(CC)COC(=O)c1ccccc1C(=O)c1ccc(-c2ccccc2)cc1]

Characterization:
GC-purity: 99%
Mass Spectroscopy (m/z): 415 (M(+)+1 285 (100%), 257, 228, 181, 152
UV-spectroscopy: λ max=287 nm (ethyl acetate)
Acid value: <2 mg KOH/g
Viscosity: 12 Pa·s at 25° C.

Example 10 (Inventive)

Synthesis of 4-Phenylbenzoyl Benzoic Acid Amyl Ester 30.2 g (0.1 mole) of 4-phenylbenzoyl benzoic acid from Example 8 was mixed with 17.6 g (0.2 moles) of amyl alcohol, 50 ml of toluene, and 2.0 g of toluene sulfonic acid. The mixture was heated to reflux and, within 3 hours, 3 ml of water was separated, and the acid value dropped below 5 mg KOH/g. The mixture was allowed to cool down to room temperature, diluted with 50 ml of methylene dichloride, and extracted three times with 100 ml of saturated sodium bicarbonate solution. Then, the solvents were removed by rotary evaporator at 80° C. (50 hPa). Then, the excess of amyl alcohol was removed under reduced pressure of 0.1 hPa at a temperature of 90° C. A light brown clear liquid remained.
Yield: 38.1 g (91% of theory)

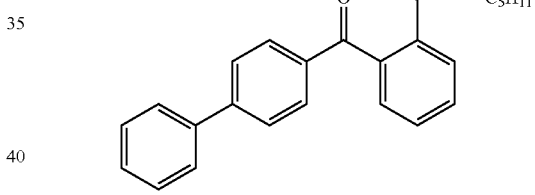

Characterization:
GC-purity: 99%
UV-spectroscopy: λ max=286 nm (ethyl acetate)
Acid value: <2 mg KOH/g
Viscosity: 13 Pa·s at 25° C.

Example 11: Synthesis of 4-Terphenoyl Benzoic Acid 22.1 g (0.1 mole) of terphenyl and 14.8 g (0.1 mole) of phthalic anhydride were dispersed in 90 ml of methylene dichloride. Then 22.0 g (0.2 mole) of aluminum trichloride was added in portions under water cooling over 15 minutes, so that the temperature did not exceed 20° C. Then the mixture was allowed to stir overnight at room temperature and got a brown color. Then, the reaction mixture was diluted with 100 ml of methylene dichloride and poured slowly under stirring into a mixture of 300 ml of water and 100 g of sulfuric acid. A white solid is formed, which is separated by filtration, washed with 4×300 ml of water and dried.
Yield: 35.5 g (94.8% of theory)

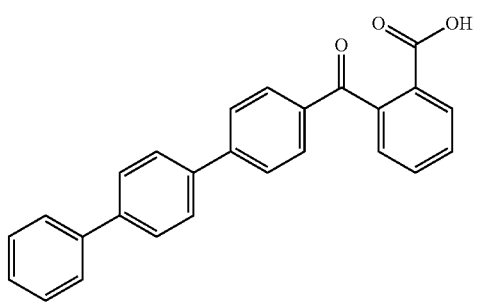 [SMILES: O=C(O)c1ccccc1C(=O)c1ccc(-c2ccc(-c3ccccc3)cc2)cc1]

Characterization:
GC-purity: 94 area % (6 area % terphenyl)
450 (M(+)−1+73(trimethylsilane) 100%, 435 (100%), 361, 257, 181
Melting point: 235-240° C.

Example 12 (Inventive)

Synthesis of 4-Terphenoyl Benzoic Acid Ethylhexyl Ester 18.9 g (0.05 mole) of 4-terphenoyl benzoic acid from previous example was mixed with 26.0 g (0.2 mole) of 2-ethylhexanol, 30 ml of xylene and 0.5 g of toluene sulfonic acid. The mixture was heated to reflux, and within 3 hours the dispersion disappeared and a clear solution was obtained, approximately 1.5 ml of water was separated and the acid value dropped below 4 mg KOH/g. The mixture was allowed to cool down to room temperature, diluted with 50 ml of methylene dichloride and extracted three times with 100 ml of saturated sodium bicarbonate solution. Then the solvents were removed by rotary evaporator at 25 to 100° C. (300-30 hPa). Then, the excess of 2-ethylhexanol was removed under reduced pressure of 0.1 hPa at a temperature of 120° C. A yellow, clear high viscosity liquid remained.
Yield: 20.1 g (78.1% of theory)

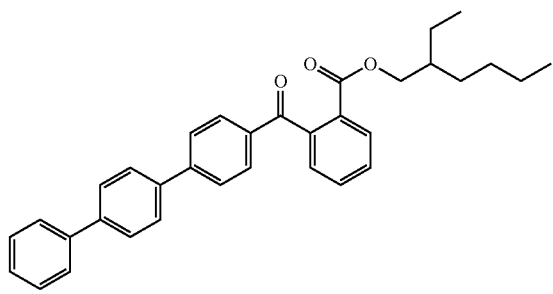 [SMILES: CCCCC(CC)COC(=O)c1ccccc1C(=O)c1ccc(-c2ccc(-c3ccccc3)cc2)cc1]

Characterization:
UV-spectroscopy: λ max=309 nm (ethyl acetate)
GC purity: 90% (4 area % terphenyl, 5 area % 2-ethylhexanol)
Mass Spectroscopy (m/z): 491 (M(+)+1, 379, 362 (100%)
Acid value: 3 mg KOH/g.

Example 13: Printing Performance of Inks Comprising 4-Arylbenzoyl Benzoic Acid Compounds Lithographic UV-inks were tested on a Didde web offset press equipped with two UV-dryers. Two cyan lithographic energy curable packaging inks (inventive and comparative) were made on a three roll mill with 3 passes at 1 MPa (25° C.), having the following composition and properties:

TABLE 6

Composition (wt. %) of two inks tested on the Didde web offset press

| Material | Inventive Ink | Comparative Ink |
|---|---|---|
| Varnish of ketone-aldehyde resin in TMPTA (48%) | 44.00 | 44.00 |
| Multifunctional acrylate monomer blend (Sun) | 18.00 | 18.00 |
| Flow agent (Tego) | 0.50 | 0.50 |
| Stabilizer (BASF) | 1.00 | 1.00 |
| Photoinitiator blend, based on aminobenzoates & benzophenone-derivatives (no 4-PBz) & aminoketones (Sun) | 10.00 | 10.00 |
| 4-phenyl-benzophenone (4-PBz) | — | 2.50 |
| 4-Phenyl benzoyl benzoic acid ethyl hexyl ester (Example 9) | 2.50 | — |
| Blue pigment 15:3 (Sun) | 21.00 | 21.00 |
| Inorganic filler (Emerys) | 3.00 | 3.00 |
| Total | 100.00 | 100.00 |
| Viscosity @ 50 s−1 [Pa · s] | 30.30 | 31.25 |

To assess print performance, both inks were tested on a Didde web offset press equipped with two UV-dryers at 800 ft/min, printed on C1S paper (coated on one side). Rycoline 4600 fountain solution was used (Sun Chemical).
Ink Duct Setting:
It determines the size of the opening through which the ink enters the ink train
Printing Speed:
The velocity of the moving web (substrate) in feet per minute
Water Window:
The water window gives a range of the fountain solution settings for which a targeted print density can be achieved. The larger the water window, the more robust lithography is anticipated. The water window test was stopped when optical density dropped by >0.1 than starting density.
Printed Optical Density:
The achieved optical density of the cured prints under the given ink duct settings and fountain settings was measured in-line with a mounted Techkon's Spectro Edge Model ES500 densitometer.
UV-Cure:
The extent of UV-cure was assessed by a thumb twist test and a solvent resistance test with isopropanol (IPA). Such a test is well known in the art and is, for example, described on page 74 of Test Methods for UV and EB Curable Systems, C. Lowe & P.K.T Oldring, SITA Technology, 1994, ISBN 0 947798 07 2.
Good cure (test passed) can be defined as the degree of cure in which no ink is transferred to the thumb and the ink has a solvent resistance of at least 10 IPA double-rubs. The press operator notes the lamp settings at which thumb twist test and solvent resistance test are passed. Only one of two dryers were used:
1 lamp low (not tested in our experiment)
1 lamp medium (good cure if all tests are passed)
1 lamp high (fair cure if all tests are passed)
Misting:
Misting is assessed at different places on the press, usually near an ink duct and a printing plate. A white piece of paper is placed at a defined distance from the ink rollers, and the press is run for a defined period of time, and defined speed and temperature. Then, the ink mist which is transferred to the paper is assessed by visual comparison to a master example or by measurement with a densitometer. Very little ink on the paper means that the ink has very low misting and low tendency to contaminate the printing press and press room with ink mist.

Visual assessment of misting can be described as follows:
Very good (ink mist is undetectable or minimal)
Good (small amount of ink mist is deposited on the paper)
Bad (large amount of ink mist is deposited on the paper)
The print performance results are shown in Table 7.

TABLE 7

Press performance of inventive and comparative ink

| Printing Press results 800 ft./min | Inventive ink | Comparative ink |
|---|---|---|
| Ink duct setting in units | 1.50 | 2.00 |
| Printing speed (feet per minute) | 800 | 800 |
| Water window in % | 14-50, 35 units | 20-50, 30 units |
| Optical density in Water window in % | 1.57/1.57/1.56/1.57/ 1.57/1.53/1.49/1.51 | 1.55/1.55/1.57/1.53/ 1.54/1.52/1.45 |
| Printed optical density in units | 1.57 | 1.55 |
| UV-cure results 1 lamp high | Fully cured; all tests passed | Fully cured; all tests passed |
| UV-cure results 1 lamp medium | Fully cured; all tests passed | Fully cured, but IPA double rubs only 8 to 9 |
| Misting properties | No misting observed | No misting observed |

Table 7 shows that the inventive ink exhibits a slightly wider water window and comparable achieved optical density vs. the comparative ink.

Overall, the inventive ink performs similarly to the comparative ink. But the inherently liquid 4-phenyl benzoyl benzoic acid ethylhexyl ester will not precipitate from the ink, in contrast to the solid 4-phenylbenzophenone, which often does precipitate. The precipitation of 4-phenylbenzophenone is sometimes an issue, affecting ink quality.

Moreover, the high melting point and the hard crystals of 4-phenylbenzophenone makes it more difficult to grind an UV-ink on a three-roll mill or a bead mill. Often, inks with high levels of 4-phenylbenzophenone need additional paths on the three roll mill, before the desired fineness of the ink is achieved, which results in higher production cost. The issue can be completely avoided by using the composition of this invention containing inherently liquid photoinitiators, such as 4-phenylbenzoyl benzoic acid ethyl hexyl ester.

The present invention has been described in detail, including the preferred embodiments thereof. However, it will be appreciated that those skilled in the art, upon consideration of the present disclosure, may make modifications and/or improvements on this invention that fall within the scope and spirit of the invention.

What is claimed is:

1. A compound of Formula 1:

$$\text{(1)}$$

wherein:

A is $C_6$-$C_{22}$ aryl or a (6- to 22-membered) heteroaryl;

$R^1$ is selected from the group consisting of H, $C_1$-$C_8$ alkyl, $C_1$-$C_8$ alkoxy, $C_3$-$C_{22}$ cycloalkyl, a (3- to 22-membered) unsaturated or partially unsaturated heterocycle, $C_6$-$C_{22}$ aryl, a (6- to 22-membered) heteroaryl, and $NR^3R^4$;

$R^3$ and $R^4$ are each independently selected from H or $C_1$-$C_8$ alkyl; or $R^3$ and $R^4$, together with the nitrogen atom to which they are attached, form a five or six membered ring;

$R^2$ is selected from the group consisting of $C_4$-$C_{22}$ alkyl, $C_7$-$C_{22}$ alkaryl, $C_7$-$C_{22}$ aralkyl, a glycol ether residue comprising a total of between five and twenty two carbon and oxygen atoms, a $C_4$-$C_{22}$ aminoalkyl, and $NR^3R^4$ optionally substituted with $C_1$-$C_8$ alkyl;

provided that when A is phenyl and $R^2$ is a glycol ether residue, methyl, ethyl, ethylhexyl, methylheptyl, benzyl, t-butylbenzyl, or methylnaphthyl, then $R^1$ is not H; and provided that when A is phenyl and $R^2$ is t-butyl, then $R^1$ is not methyl.

2. The compound of claim 1, wherein A is phenyl.

3. The compound of claim 1, wherein the compound is a $C_9$-$C_{22}$ alkyl or aralkyl ester.

4. The compound of claim 1, wherein the compound is a glycol ether ester; provided that if A is phenyl, then $R^1$ is not H.

5. The compound of claim 1, wherein the compound is an alicyclic ester.

6. The compound of claim 1, wherein the compound is a dialkylaminoalkyl ester.

7. A UV-curable ink or coating comprising as a component for radical photoinitiator systems a compound of claim 1.

8. A UV-curable ink or coating, comprising as a component for radical photoinitiator systems a compound of claim 1 and a $C_5$-$C_8$ ester of said compound.

9. A composition comprising at least one compound of claim 1 and at least one hydrogen radical donor; wherein the composition is liquid at 25° C.

10. The composition of claim 9, comprising at least one $C_5$-$C_8$ ester of a compound of Formula 1:

$$\text{(1)}$$

wherein:

A is $C_6$-$C_{22}$ aryl or a (6- to 22-membered) heteroaryl;

$R^1$ is selected from the group consisting of H, $C_1$-$C_8$ alkyl, $C_1$-$C_8$ alkoxy, $C_3$-$C_{22}$ cycloalkyl, a (3- to 22-membered) unsaturated or partially unsaturated heterocycle, $C_6$-$C_{22}$ aryl, a (6- to 22-membered) heteroaryl, and $NR^3R^4$;

$R^3$ and $R^4$ are each independently selected from H or $C_1$-$C_8$ alkyl; or $R^3$ and $R^4$, together with the nitrogen atom to which they are attached, form a five or six membered ring;

$R^2$ is selected from the group consisting of $C_4$-$C_{22}$ alkyl, $C_7$-$C_{22}$ alkaryl, $C_7$-$C_{22}$ aralkyl, a glycol ether residue comprising a total of between five and twenty two carbon and oxygen atoms, a $C_4$-$C_{22}$ aminoalkyl, and $NR^3R^4$ optionally substituted with $C_1$-$C_8$ alkyl;

provided that when A is phenyl and $R^2$ is a glycol ether residue, methyl, ethyl, ethylhexyl, methylheptyl, benzyl, t-butylbenzyl, or methylnaphthyl, then $R^1$ is not H; and provided that when A is phenyl and $R^2$ is t-butyl, then $R^1$ is not methyl.

11. The composition of claim 10, wherein the concentration of the $C_5$-$C_8$ ester compound of Formula I is greater than 10 weight %.

12. The composition of claim 10, wherein the $C_5$-$C_8$ ester compound of Formula I is an amyl ester or an ethylhexyl ester.

13. The composition of claim 9, wherein the hydrogen donor is a tertiary amine or a thioether.

14. A composition comprising at least two compounds of claim 1, wherein the at least two compounds are not liquid at 25° C. in a pure form.

15. The composition of claim 9 further comprising one or more $C_1$-$C_4$ esters of 4-arylbenzoylbenzoic acid.

16. A coating or printing ink, curable with actinic light, comprising one or more acrylates or methacrylates, a tertiary amine and at least one compound of claim 1.

17. A coating or printing ink, curable with actinic light, comprising one or more acrylates or methacrylates, a tertiary amine and the composition of claim 9.

18. A The coating or printing ink of claim 16, comprising at least one $C_5$-$C_8$ ester of a compound of Formula I:

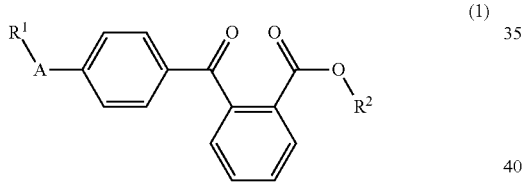

wherein:
A is $C_6$-$C_{22}$ aryl or a (6- to 22-membered) heteroaryl;
le is selected from the group consisting of H, $C_1$-$C_8$ alkyl, $C_1$-$C_8$ alkoxy, $C_3$-$C_{22}$ cycloalkyl, a (3- to 22-membered) unsaturated or partially unsaturated heterocycle, $C_6$-$C_{22}$ aryl, a (6- to 22-membered) heteroaryl, and $NR^3R^4$;
$R^3$ and $R^4$ are each independently selected from H or $C_1$-$C_8$ alkyl; or $R^3$ and $R^4$, together with the nitrogen atom to which they are attached, form a five or six membered ring;
$R^2$ is selected from the group consisting of $C_4$-$C_{22}$ alkyl, $C_7$-$C_{22}$ alkaryl, $C_7$-$C_{22}$ aralkyl, a glycol ether residue comprising a total of between five and twenty two carbon and oxygen atoms, a $C_4$-$C_{22}$ aminoalkyl, and $NR^3R^4$ optionally substituted with $C_1$-$C_8$ alkyl;
provided that when A is phenyl and $R^2$ is a glycol ether residue, methyl, ethyl, ethylhexyl, methylheptyl, benzyl, t-butylbenzyl, or methylnaphthyl, then $R^1$ is not H; and
provided that when A is phenyl and $R^2$ is t-butyl, then $R^1$ is not methyl.

19. The coating or printing ink of claim 18, wherein the at least one $C_5$-$C_8$ ester compound of Formula I is an ethylhexyl ester or an amyl ester.

20. The coating or printing ink of claim 16, wherein the acrylates or methacrylates are present at a concentration of 20-98 weight %.

21. A process for preparation of a 4-phenylbenzoic acid compound of formula (1) comprising the steps of:
a) dispersing or dissolving biphenyl and phthalic anhydride in a molar ratio of 0.95:1 to 1.05:1 in an inert solvent;
b) feeding aluminum trichloride in molar excess to phthalic anhydride, so that the temperature does not exceed 20° C.;
c) stirring at 25° C. or above for at least 6 hours;
d) pouring the reaction mixture in acidified water having a pH<1; and
e) filtering off the solid precipitate, washing with water, and drying.

22. A composition comprising a 4-phenylbenzoylbenzoic acid amyl ester of formula (1), wherein the composition is liquid at 25° C.

23. A composition comprising a 4-phenylbenzoylbenzoic acid ethylhexyl ester of formula (1), wherein the composition is liquid at 25° C.

24. The coating or printing ink of claim 17, comprising at least one $C_5$-$C_8$ ester of a compound of Formula 1:

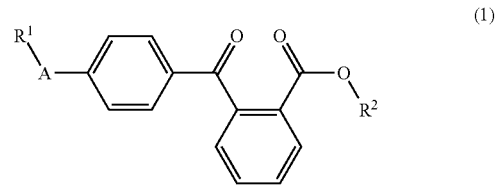

wherein:
A is $C_6$-$C_{22}$ aryl or a (6- to 22-membered) heteroaryl;
$R^1$ is selected from the group consisting of H, $C_1$-$C_8$ alkyl, $C_1$-$C_8$ alkoxy, $C_3$-$C_{22}$ cycloalkyl, a (3- to 22-membered) unsaturated or partially unsaturated heterocycle, $C_6$-$C_{22}$ aryl, a (6- to 22-membered) heteroaryl, and $NR^3R^4$;
$R^3$ and $R^4$ are each independently selected from H or $C_1$-$C_8$ alkyl; or $R^3$ and $R^4$, together with the nitrogen atom to which they are attached, form a five or six membered ring;
$R^2$ is selected from the group consisting of $C_4$-$C_{22}$ alkyl, $C_7$-$C_{22}$ alkaryl, $C_7$-$C_{22}$ aralkyl, a glycol ether residue comprising a total of between five and twenty two carbon and oxygen atoms, a $C_4$-$C_{22}$ aminoalkyl, and $NR^3R^4$ optionally substituted with $C_1$-$C_8$ alkyl;
provided that when A is phenyl and $R^2$ is a glycol ether residue, methyl, ethyl, ethylhexyl, methylheptyl, benzyl, t-butylbenzyl, or methylnaphthyl, then $R^1$ is not H; and
provided that when A is phenyl and $R^2$ is t-butyl, then $R^1$ is not methyl;
wherein wherein the composition is liquid at 25° C.

25. The coating or printing ink of claim 24, wherein the $C_5$-$C_8$ ester compound of Formula I is an ethylhexyl ester or an amyl ester.

* * * * *